(12) United States Patent
Choi et al.

(10) Patent No.: US 10,174,327 B2
(45) Date of Patent: Jan. 8, 2019

(54) RNA OLIGONUCLEOTIDE AND IMMUNE SYSTEM ENHANCER COMPRISING SAME

(71) Applicant: KOREA ADVANCED INSTITUTE OF SCIENCE AND TECHNOLOGY, Daejeon (KR)

(72) Inventors: Byong-Seok Choi, Daejeon (KR); Mi Kyung Lee, Daejeon (KR); Janghyun Lee, Daejeon (KR); Suk-Jo Kang, Daejeon (KR); Eun Byeol Park, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 49 days.

(21) Appl. No.: 15/165,992

(22) Filed: May 26, 2016

(65) Prior Publication Data
US 2017/0107518 A1   Apr. 20, 2017

(51) Int. Cl.
*A61K 31/713* (2006.01)
*A61K 48/00* (2006.01)
*C12N 15/117* (2010.01)

(52) U.S. Cl.
CPC ........ *C12N 15/117* (2013.01); *C12N 2310/17* (2013.01); *C12N 2310/315* (2013.01); *C12N 2310/317* (2013.01); *C12N 2310/52* (2013.01); *C12N 2310/533* (2013.01)

(58) Field of Classification Search
CPC .............. C12N 15/117; C12N 2310/17; C12N 2310/50; A61K 31/713; A61K 48/00
USPC .... 435/6.1, 91.1, 91.31, 455, 458; 536/23.1, 536/24.5
See application file for complete search history.

(56) References Cited

U.S. PATENT DOCUMENTS

| | | | |
|---|---|---|---|
| 7,691,997 B2* | 4/2010 | Khvorova | A61K 31/713 536/24.5 |
| 2012/0121551 A1 | 5/2012 | Hartmann et al. | 424/93.7 |
| 2012/0288476 A1 | 11/2012 | Hartmann et al. | 424/85.4 |
| 2015/0148530 A1* | 5/2015 | McSwiggen | C12N 15/1131 536/24.5 |
| 2017/0051056 A1* | 2/2017 | Naka | G01N 33/57449 |

OTHER PUBLICATIONS

U.S. Appl. No. 15/310,559.*
Kim et al, Nature Biotech., vol. 22, No. 3, pp. 321-325 (2004).*
Samuel, C.E., Nature Biotech., vol. 22, No. 3, pp. 280-282 (2004).*
Hwang S., et al., (2012). "5'-Triphosphate-RNA-independent activation of RIG-I via RNS aptamer with enhanced antiviral activity", *Nucleic Acids Research* 40(6):2724-2733.

* cited by examiner

*Primary Examiner* — Jane J Zara
(74) *Attorney, Agent, or Firm* — Harness, Dickey & Pierce, P.L.C.

(57) ABSTRACT

The present disclosure provides an RNA oligonucleotide having a helical bend structure and a use thereof. Specifically, double strands formed by a complementary binding of two sequences have a helical bend structure in the RNA oligonucleotide. The RNA oligonucleotide can increase the expression of interferon-β or ISG56 and thus can be used as an immune system enhancer.

17 Claims, 7 Drawing Sheets

Specification includes a Sequence Listing.

```
                        SEQUENCE LISTING

<160> NUMBER OF SEQ ID NOS: 19

<210> SEQ ID NO 1
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: A, G, C or U
<220> FEATURE:
<221> NAME/KEY: misc_feature
<222> LOCATION: (7)..(8)
<223> OTHER INFORMATION: A, G, C or U

<400> SEQUENCE: 1 nguagann                                                                 8

<210> SEQ ID NO 2
<211> LENGTH: 8
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(2)
<223> OTHER INFORMATION: A, G, C or U
<220> FEATURE:
<221> NAME/KEY: misc_feature
<222> LOCATION: (8)..(8)
<223> OTHER INFORMATION: A, G, C or U

<400> SEQUENCE: 2 nnuuugcn                                                                 8

<210> SEQ ID NO 3
<211> LENGTH: 8
<212> TYPE: RNA
<213> ORGANISM: Artificial Sequence
<220> FEATURE:
<223> OTHER INFORMATION: RNA oligonucleotide

<400> SEQUENCE: 3 gguagacg                                                                 8

<210> SEQ ID NO 4
<211> LENGTH: 8
```

```
<212> TYPE: RNA
<213> ORGANISM: Artificial Sequence
<220> FEATURE:
<223> OTHER INFORMATION: RNA oligonucleotide

<400> SEQUENCE: 4 cguuugcc                                                                 8

<210> SEQ ID NO 5
<211> LENGTH: 34
<212> TYPE: RNA
<213> ORGANISM: Artificial Sequence
<220> FEATURE:
<223> OTHER INFORMATION: control RNA oligonucleotide

<400> SEQUENCE: 5
gagcagaaac aaggcuucgg ccuuguuucu gcuc                                   34

<210> SEQ ID NO 6
<211> LENGTH: 33
<212> TYPE: RNA
<213> ORGANISM: Artificial Sequence
<220> FEATURE:
<223> OTHER INFORMATION: iav RNA oligonucleotide

<400> SEQUENCE: 6
gaguagaaac aaggcuucgg ccugcuuuug cuc                                    33

<210> SEQ ID NO 7
<211> LENGTH: 80
<212> TYPE: RNA
<213> ORGANISM: Artificial Sequence
<220> FEATURE:
<223> OTHER INFORMATION: Int-NS1 RNA oligonucleotide

<400> SEQUENCE: 7
aguagaaaca aggguguuuu uuauuauuaa auaagcugaa guguuuggau ccauuauguc        60
uuugucaccc ugcuuuugcu                                                   80

<210> SEQ ID NO 8
<211> LENGTH: 32
<212> TYPE: RNA
<213> ORGANISM: Artificial Sequence
<220> FEATURE:
<223> OTHER INFORMATION: Bend-GC RNA oligonucleotide

<400> SEQUENCE: 8
gguagacgcg cgcguucgcg cgcgcguuug cc                                     32

<210> SEQ ID NO 9
<211> LENGTH: 20
<212> TYPE: RNA
<213> ORGANISM: Artificial Sequence
<220> FEATURE:
<223> OTHER INFORMATION: Cont-GC-8bp RNA oligonucleotide

<400> SEQUENCE: 9
ggcagacguu cgcgucugcc                                                   20

<210> SEQ ID NO 10
<211> LENGTH: 20
<212> TYPE: RNA
<213> ORGANISM: Artificial Sequence
<220> FEATURE:
<223> OTHER INFORMATION: Bend-GC-8bp RNA oligonucleotide
```

-continued

```
<400> SEQUENCE: 10
gguagacguu cgcguuugcc                                          20

<210> SEQ ID NO 11
<211> LENGTH: 18
<212> TYPE: DNA
<213> ORGANISM: Artificial Sequence
<220> FEATURE:
<223> OTHER INFORMATION: interferon-beta forward primer

<400> SEQUENCE: 11
ggaggacgcc gcattgac                                            18

<210> SEQ ID NO 12
<211> LENGTH: 24
<212> TYPE: DNA
<213> ORGANISM: Artificial Sequence
<220> FEATURE:
<223> OTHER INFORMATION: interferon-beta reverse primer

<400> SEQUENCE: 12
caatagtctc attccagcca gtgc                                     24

<210> SEQ ID NO 13
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 13
gcattgccct caacgaccac                                          20

<210> SEQ ID NO 14
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 14
gaggccatgt gggccatgag                                          20

<210> SEQ ID NO 15
<211> LENGTH: 22
<212> TYPE: DNA
<213> ORGANISM: Artificial Sequence
<220> FEATURE:
<223> OTHER INFORMATION: ISG56 forward primer

<400> SEQUENCE: 15
gcctccttgg gttcgtctac aa                                       22

<210> SEQ ID NO 16
<211> LENGTH: 22
<212> TYPE: DNA
<213> ORGANISM: Artificial Sequence
<220> FEATURE:
<223> OTHER INFORMATION: ISG56 reverse primer

<400> SEQUENCE: 16
tcaaagtcag cagccagtct ca                                       22

<210> SEQ ID NO 17
<211> LENGTH: 16
```

```
<212> TYPE: RNA
<213> ORGANISM: Artificial Sequence
<220> FEATURE:
<223> OTHER INFORMATION: RNA oligonucleotide
<220> FEATURE:
<221> NAME/KEY: misc_feature
<222> LOCATION: (1)..(1)
<223> OTHER INFORMATION: A, G, C or U
<220> FEATURE:
<221> NAME/KEY: misc_feature
<222> LOCATION: (7)..(10)
<223> OTHER INFORMATION: A, G, C or U
<220> FEATURE:
<221> NAME/KEY: misc_feature
<222> LOCATION: (16)..(16)
<223> OTHER INFORMATION: A, G, C or U

<400> SEQUENCE: 17
nguagannnn uuugcn                                                 16

<210> SEQ ID NO 18
<211> LENGTH: 16
<212> TYPE: RNA
<213> ORGANISM: Artificial Sequence
<220> FEATURE:
<223> OTHER INFORMATION: RNA oligonucleotide

<400> SEQUENCE: 18
gguagacgcg uuugcc                                                 16

<210> SEQ ID NO 19
<211> LENGTH: 89
<212> TYPE: RNA
<213> ORGANISM: Artificial Sequence
<220> FEATURE:
<223> OTHER INFORMATION: Long_Bend RNA oligonucleotide

<400> SEQUENCE: 19
gguagacgaa accagauaaa aaaaaaaaaa aaaaaaaaaa aaauaauuuu uuuuuuuuuu    60
uuuuuuuuuu uuaucugguu ucguuugcc                                     89
```

RNA OLIGONUCLEOTIDE AND IMMUNE SYSTEM ENHANCER COMPRISING SAME

CROSS-REFERENCE TO RELATED APPLICATIONS

This application claims the benefit and priority of Korean Patent Application No. 10-2015-0144306 filed on Oct. 15, 2015 and Korean Patent Application No. 10-2016-0031309 filed on Mar. 16, 2016. The entire disclosure of the above applications is incorporated herein by references.

FIELD

The present disclosure relates to an RNA oligonucleotide having a particular sequence and structure, and an immune system enhancer comprising same.

BACKGROUND

Interferon is a glycoprotein derived from most of the cells having a nucleus, and regulates immune responses. Interferon elicits a series of intracellular responses and immunoregulatory responses by binding to a specific receptor on the cell surface of the cell membrane. The intracellular responses may include induction of the activation of specific enzymes, etc., and the immunoregulatory responses may include enhancing the phagocytosis activity of macrophages and the cytotoxicity of lymphocytes against target cells.

Interferons are classified into type 1 and type 2 based on the physiochemical and functional properties. Type 1 interferons include interferon-$\alpha$, -$\beta$, -$\tau$, and -$\omega$; and type 2 interferons include interferon-$\gamma$. Among them, interferon-$\beta$ is a protein of a single chain, which has a molecular weight of approximately 20 kDa, contains a sugar of about 20%, and is composed of 166 amino acids.

Currently, recombinant interferon-$\beta$ is used as a therapeutic agent or adjuvant for a variety of diseases and, the representative disease for which interferon-$\beta$ is used as a therapeutic agent is multiple sclerosis, an autoimmune disease (Airas L. et al., *Ann NY Acad Sci.*, 2007, September: 1110:641-8).

Recently, researches have been made to enhance immune responses using an RNA oligonucleotide. U.S. Patent Application Publication No. 2012/0288476 discloses that an uncapped oligonucleotide having a phosphate group at the 5'-end can enhance the expression of type 1 interferon, interleukin-18, and interleukin-1$\beta$, etc.

In addition, U.S. Patent Application Publication No. 2012/0121551 discloses that RNAs consisting of four nucleotides can promote immune responses by inducing the activation of interferon-$\alpha$.

The RNAs disclosed above have the common feature that they have a triphosphate group at the 5'-end. It is known that an RNA which does not contain a cap but has a triphosphate group at the 5'-end can activate the expression of interferon by binding to intracellular retinoic acid-inducible gene-I (RIG-I) protein.

The present inventors have endeavored diligently to find a substance which can increase the expression of interferon-$\beta$ or interferon stimulated gene 56 (ISG56) expressed by interferon-$\beta$, and surprisingly and unexpectedly discovered that an RNA oligonucleotide which does not have a triphosphate group at the 5'-end can also increase the expression of interferon-$\beta$ or ISG56 if the RNA oligonucleotide has a specific sequence and structure, and thus can be used as an immune system enhancer.

SUMMARY

An object of the present disclosure is to provide an RNA oligonucleotide having a specific sequence and structure, and an immune system enhancer comprising the RNA oligonucleotide as an active ingredient.

The present disclosure provides an RNA oligonucleotide comprising the base sequence represented by SEQ ID NO:1 (5'-$N_1$GUAGAN$_2$N$_3$-3') and the base sequence represented by SEQ ID NO:2 (5'-$N_4$N$_5$UUUGCN$_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

The present disclosure also provides an RNA oligonucleotide comprising the base sequence represented by SEQ ID NO:1 (5'-$N_1$GUAGAN$_2$N$_3$-3') and the base sequence represented by SEQ ID NO:2 (5'-$N_4$N$_5$UUUGCN$_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

The present disclosure also provides an RNA oligonucleotide comprising the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-$N_4$N$_5$UUUGCN$_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

The present disclosure also provides an RNA oligonucleotide comprising the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-$N_4$N$_5$UUUGCN$_6$-3') wherein first and second base sequences represented by SEQ ID NO:17 are bound to each other by a complementary binding to form double strands having a helical bend structure; and the 3'-end of the first base sequence represented by SEQ ID NO:17 and the 5'-end of the second base sequence represented by SEQ ID NO:17 are connected into a loop to form a hairpin structure; and the 5'-end of the first base sequence represented by SEQ ID NO:17 has a hydroxy (OH) group.

The present disclosure also provides an immune system enhancer comprising the aforementioned RNA oligonucleotide as an active ingredient.

When a cell line is treated with an RNA oligonucleotide having a specific sequence and helical bend structure according to the present disclosure, the expression of interferon-$\beta$ or ISG56 is increased. Thus, a composition comprising the RNA oligonucleotide can be used as an immune system enhancer.

DETAILED DESCRIPTION

Figure 1:
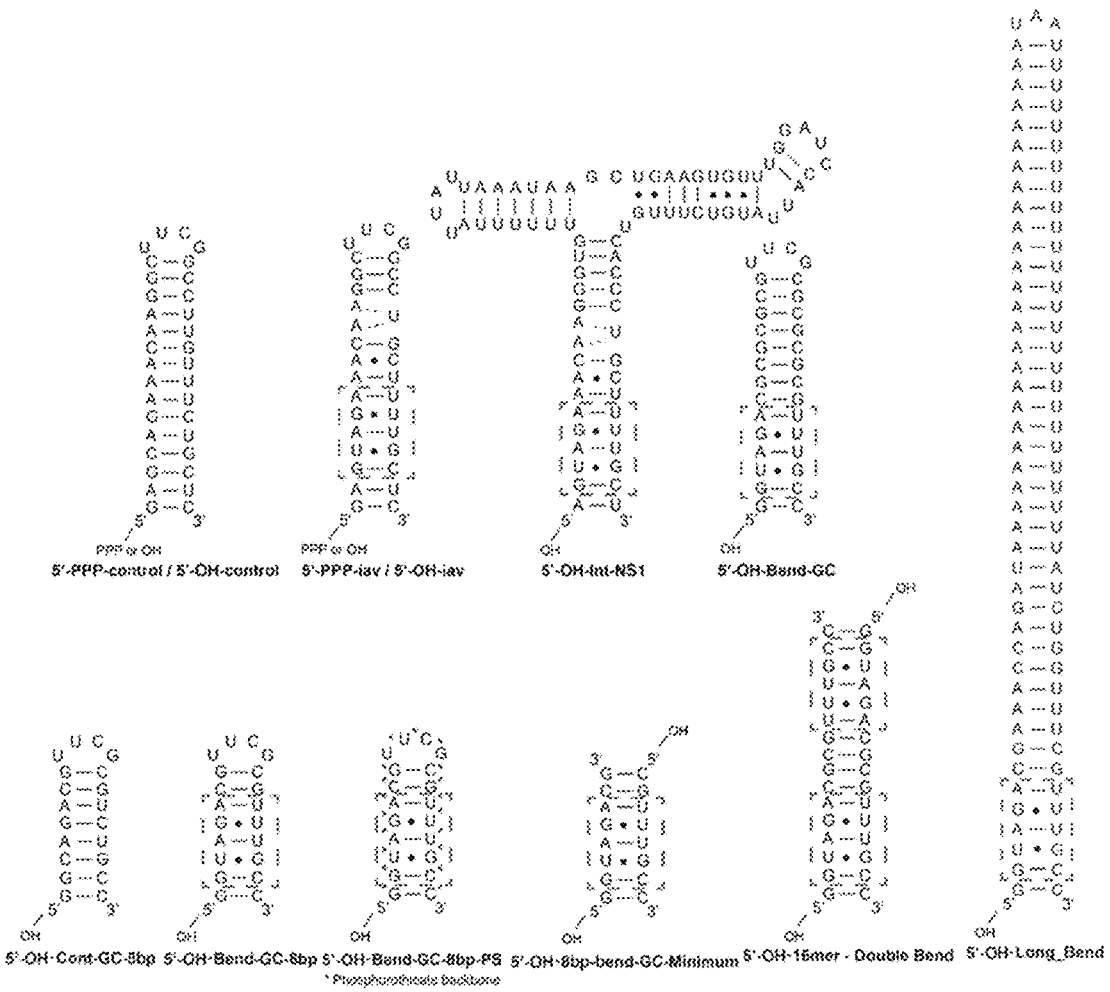
FIG. 1 shows the sequences and structures of RNA oligonucleotides prepared according to one example of the present disclosure.

Hereinafter, the present invention will be described in detail.

The present disclosure provides an RNA oligonucleotide comprising the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; and the base sequences represented by SEQ ID NO:1 and SEQ ID NO:2 have a hydroxy (OH) group at the 5'-end thereof.

An RNA oligonucleotide according to the present disclosure may have 8 to 100, 8 to 50, 8 to 30, 8 to 20, 10 to 100, 10 to 50, 10 to 30, 20 to 500, 20 to 300, 10 to 200, 10 to 100, or 20 to 50 bases. An RNA oligonucleotide in one example of the present disclosure may have 8 to 16 bases when it is a single strand, while it may have 16 to 32 bases when double strands.

As used herein, the term "complementary binding" refers to the formation of a duplex structure of one or two oligonucleotides in which complementary base sequences are paired to form a hairpin or double helix structure. The complementary binding may be formed by Watson-Crick pairing between complementary nucleotide sequences. The complementary binding may also be formed even when some Non-Watson-Crick base pairs are present.

In the base sequence represented by SEQ ID NO:1 or SEQ ID NO:2 which forms the RNA oligonucleotide, $N_1$ to $N_6$ may be one selected from the group consisting of A, G, C and U. Specifically, $N_1$ to $N_6$ may be G or C. In one example of the present disclosure, $N_1$ may be G, $N_2$ may be C, and $N_3$ may be G in the base sequence represented by SEQ ID NO:1 (corresponding to SEQ ID NO:3); and $N_4$ may be C, $N_5$ may be G, and $N_6$ may be C in the base sequence represented by SEQ ID NO:2 (corresponding to SEQ ID NO:4).

When the RNA oligonucleotide having such base sequences form a double strand, the third base (U) and the fifth base (G) of the base sequence of SEQ ID NO:1 and the sixth base (G) and the fourth base (U) of the base sequence of SEQ ID NO:2 respectively form wobble base pairs, or non-Watson-Crick base pairs.

An RNA oligonucleotide of the present disclosure may form a helical bend structure between the fourth base (A) of the base sequence of SEQ ID NO:1 and the fifth base (U) of the base sequence of SEQ ID NO:2.

In one example of the present disclosure, the helical bend structure is formed between the fourth base (A) of the base sequence of SEQ ID NO:1 and the fifth base (U) of the base sequence of SEQ ID NO:2 when the third base (U) and the fifth base (G) of the base sequence of SEQ ID NO:1 and the sixth base (G) and the fourth base (U) of the base sequence of SEQ ID NO:2 respectively form wobble base pairs.

The helical bend structure may have a shape bent in 10 to 90 degrees relative to the plane formed by the double-stranded RNA, particularly 30 to 70 degrees, and more particularly 40 to 50 degrees.

In the RNA oligonucleotide according to the present disclosure, at least one of the phosphodiester bonds in the RNA oligonucleotide may be changed to at least one selected from the group consisting of a phosphorothioate bond, a boranophosphate bond and a methylphosphonate bond, in order to inhibit degradation by endonuclease and improve in vivo stability. In a specific example of the present disclosure, at least one of the phosphodiester bonds may be changed to the phosphorothioate bond.

Also, the present disclosure provides an RNA oligonucleotide comprising the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein the base sequences are bound to each other by a complementary binding to form double strands having a helical bend structure; the 3'-end of the base sequence represented by SEQ ID NO:1 and the 5'-end of the base sequence represented by SEQ ID NO:2 are connected into a loop to form a hairpin structure; and the base sequence represented by SEQ ID NO:1 has a hydroxy (OH) group at the 5'-end thereof.

An RNA oligonucleotide having the hairpin structure of the present disclosure may have the characteristics described above. A phosphodiester bond constituting the RNA oligonucleotide may be substituted with another bond described above.

In the hairpin structure, the loop may be composed of 4 to 80, 4 to 75, 4 to 70, 4 to 65, 4 to 60, 4 to 55, 4 to 50, 4 to 45, 4 to 40, 4 35, 4 to 30, 4 to 25, 4 to 20, 4 to 15, or 4 to 10 bases. In one example of the present disclosure, the loop may be composed of 4, 15, 16, 64 or 73 bases.

Also, if some of the base sequences constituting the loop are complementary to each other, they may form a stem structure with Watson-Crick base pairing. The stem structure may include AU motif in which A and U forms a Watson-Crick base pair.

In one example of the present disclosure, the four bases constituting the loop are UUCG.

In one example of the present disclosure, the RNA oligonucleotide having the hairpin structure may be the base sequence represented by SEQ ID NO:6, SEQ ID NO:7, SEQ ID NO:8, SEQ ID NO:10 or SEQ ID NO:19.

Also, the present disclosure provides an RNA oligonucleotide comprising the base sequence represented by SEQ ID NO:17 (5'-$N_1$GUAGA$N_2N_3N_4N_5$UUUGC$N_6$-3') formed by connecting the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein two base sequences represented by SEQ ID NO:17 are bound to each other by a complementary binding to form double strands having a helical bend structure; and the base sequence represented by SEQ ID NO:17 has a hydroxy (OH) group at the 5'-end thereof.

Specifically, the RNA oligonucleotide may have two base sequences represented by SEQ ID NO:17 with a palindromic structure. The term "palindromic structure" refers to a structure in which two base sequences constituting double strands are composed of identical base sequence when read from the 5'- to 3'-end. In the present disclosure, such palindromic structure may be double strands in which the 3'-end of the base sequence represented by SEQ ID NO:1 and the 5'-end of the base sequence represented by SEQ ID NO:2 are connected to form a single strand, and such two single strands are bound to each other by a complementary binding to form double strands. In one example of the present disclosure, such single strand may be a base sequence represented by SEQ ID NO:18.

The RNA oligonucleotide having the palindromic structure may have two helical bend structures.

Also, the RNA oligonucleotide having the palindromic structure may have the characteristics described above. A phosphodiester bond constituting the RNA oligonucleotide may be substituted with another bond described above.

Also, the present disclosure provides an RNA oligonucleotide comprising the base sequence represented by SEQ ID NO:17 (5'-$N_1$GUAGAN$_2$N$_3$N$_4$N$_5$UUUGCN$_6$-3') formed by connecting the base sequence represented by SEQ ID NO:1 (5'-$N_1$GUAGAN$_2$N$_3$-3') and the base sequence represented by SEQ ID NO:2 (5'-N$_4$N$_5$UUUGCN$_6$-3') wherein first and second base sequences represented by SEQ ID NO:17 are bound to each other by a complementary binding to form double strands having a helical bend structure; and the 3'-end of the first base sequence represented by SEQ ID NO:17 and the 5'-end of the second base sequence represented by SEQ ID NO:17 are connected into a loop to form a hairpin structure; and the 5'-end of the first base sequences represented by SEQ ID NO:17 has a hydroxy (OH) group.

An RNA oligonucleotide with such a hairpin structure may have the palindromic structure described above, and two helical bend structures. Such RNA oligonucleotide may have the characteristics described above. Also, a phosphodiester bond constituting the RNA oligonucleotide may be substituted with another bond described above.

An RNA oligonucleotide according to the present disclosure can strengthen immune functions by increasing the in vivo expression of interferon-β or ISG56, and thus it can be used as an immune system enhancer.

An immune system enhancer of the present disclosure may comprise an RNA oligonucleotide of the present disclosure as an active ingredient in an amount of 10 to 95 weight % based on the total weight of the composition. In addition, an immune system enhancer of the present disclosure may comprise one or more other active ingredients with the same or similar function in addition to the aforementioned active ingredient.

An immune system enhancer of the present disclosure may comprise one or more pharmaceutically acceptable carriers for the administration in addition to the aforementioned active ingredient. Such immune system enhancer may be formulated as a pharmaceutical composition.

The dosage of an immune system enhancer of the present disclosure may be adjusted based on various factors such as type and severity of a disease, type and amount of an active ingredient and other ingredients comprised in the composition, type of a formulation, and age, weight, general health condition, sex and diet of the patient, time of administration, route of administration and secretion rate of a composition, treatment period, and drugs simultaneously used, etc. However, to achieve a desired effect, the effective amount of an RNA oligonucleotide of the present disclosure is adjusted to reach the cell concentration of 1 to 1,000 nM, specifically 100 to 500 nM. It may be administered in a single dose or divided doses per day.

In addition, an immune system enhancer of the present disclosure may be administered to a subject by various methods known in the art. The route of administration can be appropriately selected by taking into consideration the factors such as administration method, volume of body fluid and viscosity.

The present inventors have prepared RNA oligonucleotides having a double-stranded RNA or hairpin RNA structure (FIG. 1). Among them, 5'-OH-iav or 5'-PPP-iav were found to have a helical bend structure (FIG. 2) and to increase the expression of interferon-β and ISG56 (FIGS. 3 to 7).

Accordingly, an RNA oligonucleotide having a helical bend structure of the present disclosure can increase the expression of interferon-β or ISG56, and thus it can be used as an immune system enhancer.

Hereinafter, the present invention is explained in detail by Examples and Experimental Examples. The following Examples and Experimental Examples are intended to further illustrate the present invention without limiting its scope.

Example 1. Preparation of RNA Oligonucleotides

RNA oligonucleotides which can increase the expression of interferon-β or ISG56 were prepared.

First, RNA oligonucleotides composed of the base sequence represented by SEQ ID NO:5 or SEQ ID NO:6 which have a triphosphate group at the 5'-end were prepared by the techniques known in the art. On the other hand, RNA oligonucleotides composed of one of the base sequences represented by SEQ ID NOs:3 to 10 and SEQ ID NOs:18 to 19 which have a hydroxy (OH) group at the 5'-end, or RNA oligonucleotides wherein a phosphodiester bond is substituted with a phosphorothioate bond were custom-made at Integrated DNA Technologies or Dharmacon.

As shown in FIG. 1, 5'-OH-control and 5'-PPP-control RNA oligonucleotides were prepared, which are composed of the base sequence of SEQ ID NO:5. They have a hydroxy group and a triphosphate group at the 5'-ends, respectively. In addition, 5'-OH-iav and 5'-PPP-iav RNA oligonucleotides were prepared, which are composed of the base sequence of SEQ ID NO:6, and have a hydroxy group and a triphosphate group at the 5'-ends, respectively. In addition, 5'-OH-Int-NS1 and 5'-OH-Bend-GC RNA oligonucleotides were prepared, which are composed of the base sequence of SEQ ID NO:7 or 8, respectively and have a hydroxy group at the 5'-ends. In addition, 5'-OH-Cont-GC-8bp RNA oligonucleotide was prepared, which is composed of the base sequence of SEQ ID NO:9 and has a hydroxy group at the 5'-end. In addition, an RNA oligonucleotide composed of the base sequence represented by SEQ ID NO:10 and having a hydroxy group at the 5'-end was prepared. In addition, an RNA oligonucleotide composed of the base sequence represented by SEQ ID NO:10 and having a hydroxy group at the 5'-end, wherein a phosphodiester bond forming the RNA oligonucleotide is substituted with a phosphorothioate bond was also prepared. In addition, 5'-OH-8bp-Bend-GC-Minimum RNA oligonucleotide was prepared, which is composed of the base sequences of SEQ ID NO:3 and SEQ ID NO:4, and each of the base sequences has a hydroxy group at the 5'-end, wherein the bases are bound to each other by a complementary binding to form double strands. In addition, 5'-0H-16mer-Double Bend RNA oligonucleotide was prepared, wherein two base sequences represented by SEQ ID NO:18 are bound to each other by a complementary binding to form double strands and each of the base sequences represented by SEQ ID NO:18 has a hydroxy (OH) group at the 5'-end. In addition, 5'-OH-Long_Bend RNA oligonucleotide was prepared, which is composed of the base sequence of SEQ ID NO:19, and has a hydroxy group at the 5'-end.

Example 2. Verification of Structure of RNA Oligonucleotides

To verify the structures of the 5'-OH-iav and 5'-PPP-iav RNA oligonucleotides prepared in Example 1, the following experiments were carried out.

First, the RNA oligonucleotides prepared in Example 1 were dissolved in a buffer solution containing 10 mM sodium phosphate (pH 6.5), 0.01 mM EDTA, 10 (v/v) % $D_2O$ to prepare a sample, and various spectroscopic experiments were carried out by the methods known in the art. More particularly, two-dimensional NOE spectroscopy (NOESY) was carried out by a nuclear magnetic resonance (NMR) spectroscope (Bruker, USA) of 400, 600 and 800 MHz with the mixing time of 100 and 200 ms. Also, the following experiments were performed: $^1H$-$^{15}N$ heteronuclear single quantum coherence (HSQC) spectroscopic experiment at the temperature of 278 K, double quantum filtered correlated (DQF-COSY) and homonuclear total correlation (TOCSY) spectroscopic experiments with the mixing time of 125 ms, $^1H$-$^{31}P$ heteronuclear correlation (HET-COR) and $^1H$-$^{31}P$ Hetero-TOCSY spectroscopic experiments with the mixing time of 30 ms, and NOESY spectroscopic experiment with the mixing time of 80, 150 and 250 ms. In addition, $^1H$-$^{13}C$ CT-HSQC, HCCH-COSY, 2D HCCH-relayed COSY, 2D HCCH-TOCSY and 3D HCCH-TOCSY spectroscopic experiments were carried out.

As a result of the NMR spectroscopic experiments, the NMR peaks of hydrogens of bases of the RNA oligonucleotides and H1', H2', H3', H4', and H5'/H5" were determined. From the NOESY spectroscopic experiment, approximately 563 NOE distance constraints were obtained, which were divided into 3 to 4 groups according to the distance (e.g., 1.8 to 3.4 Å, 1.8 to 5.0 Å and 3.8 to 7.0 Å; or 1.8 to 3.4 Å, 2.5 Å to 4.5, 3.5 to 6.0 Å and 4.0 to 7.0 Å). As for non-Watson-Crick bonds, no constraints on the hydrogen bonds were used. From the $^3J_{H1', H2'}$ value obtained in DQF-COSY, δ dihedral angle was obtained, and every χ dihedral angle was fixed at −158±15 degrees. Other dihedral angles (for example, α, β, γ, ε, and ζ) were confined to the A-type helical structure of RNA. As for bulge parts, no constraints on the dihedral angles were used except for several β and ε dihedral angles. Residual dipolar coupling values were measured by HSQC experiment whose sensitivity was increased to reach the accuracy of ±1 Hz. In addition, by analyzing the result of the alignment tensor by singular value decomposition, the anisotropy value of −8.0 Hz and the rhombicity value of 0.32 were obtained. Calculation of every structure was carried out by X-PLOR 3.1 and CNS. 100 structures were generated according to the distance constraints, and simulated annealing process was carried out in which the structures were simulated at 3,000 K for 10 ps, and then cooled at 300 K for 50 ps. The distance force constant was kept at 50 kcal/mol/Å, and the dihedral angle constant was changed from 20 kcal/mol/Å to 400 kcal/mol/Å. The structures with the lowest energy state were purified at 300 K for 20 ps, and the last 5 ps were used for a retained energy minimization. A total of 220 structures obtained from the above procedure were purified by adding 22 residual dipolar coupling values, with the force constant of the residual dipolar coupling value being kept to 3.0 kcal/mol. Ultimately, 32 structures were obtained, which were analyzed by Insight II (Biosym Technologies, USA) and CURVES 5.2 software.

Figure 2:
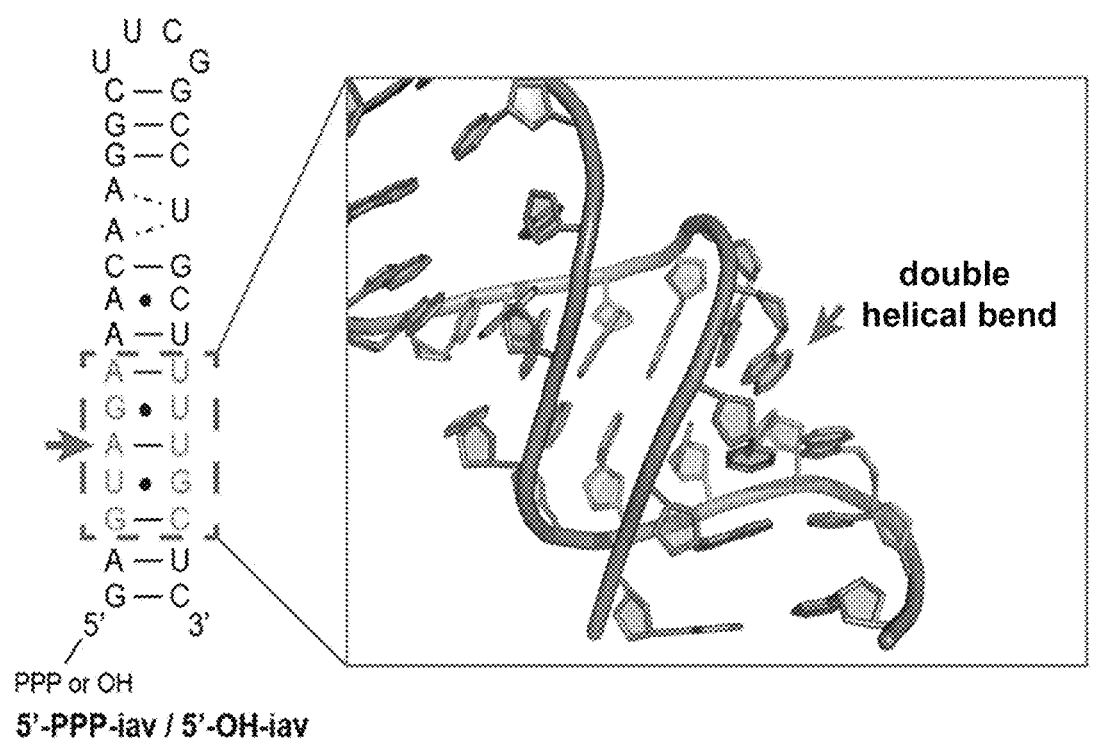
FIG. 2 shows the structure of 5'-OH-iav or 5'-PPP-iav, an RNA oligonucleotide prepared according to one example of the present disclosure.

As a result, as shown in FIG. 2, 5'-PPP-iav and 5'-OH-iav RNA oligonucleotides were found to form a helical bend structure. Such a helical bend structure was found to be generated by the formation of double strands through non-Watson-Crick base pairing between two single strands which are respectively composed of 5'-GUAGA-3' and 5'-UUUGC-3' sequences in the 5'-PPP-iav and 5'-OH-iav RNA oligonucleotides. Thus, it is understood that RNA oligonucleotides comprising the 5'-GUAGA-3' and 5'-UUUGC-3' sequences of the present disclosure, such as 5'-OH-Int-NS1, 5'-OH-Bend-GC, 5'-OH-Bend-GC-8bp, 5'-OH-Bend-GC-8bp-PS, 5'-OH-8bp-Bend-GC-Minimum, 5'-OH-16mer-Double Bend and 5'-OH-Long_Bend, also form a helical bend structure.

Experimental Example 1: Verification of Interferon-β Expression by RNA Oligonucleotides It was elucidated whether RNA oligonucleotides having a helical bend structure prepared in Example 1 increased the expression of interferon-β.

1.1. Preparation of Cell Line

First, $3 \times 10^6$ of HEK293T cells (ATCC, USA) were aliquoted into 7 ml of Dulbecco's modified Eagle's medium (DMEM) supplemented with 10% fetal bovine serum (FBS, Gibco, USA) in 100 mm tissue culture plates, and cultured for 24 hours under the condition of 37° C. and 5% $CO_2$ to prepare a cell line.

1.2. Treatment with RNA Oligonucleotides

The cell line prepared in Experimental Example 1.1. was treated with the RNA oligonucleotides prepared in Example 1.

First, the cultured cells were detached by treatment with trypsin-EDTA (Gibco, USA) and the detached cells were counted and aliquoted into 6-well plates at $1 \times 10^3$ cells/well. Then, the cells were cultured for 42 hours under the condition of 37° C. and 5% $CO_2$. After removing the medium, the cells were treated with 400 μl of OPTI-MEM without containing FBS, and the RNA oligonucleotides.

RNA oligonucleotide treatment was as follows: each 1 μM of 5'-PPP-control, 5'-PPP-iav, 5'-OH-control, 5'-OH-iav, 5'-OH-Int-NS1 and 5'-OH-Bend-OH-GC was mixed with 4 μl of lipofectamine LTX and 1.6 μl of plus-reagent, and 200 μl of resulting mixtures were added to the cells, respectively. Thereafter the cells were incubated for 4 hours under the condition of 37° C. and 5% $CO_2$. The cells for positive control were treated with poly (I:C), known as RIG-I ligand, and those for negative control were treated with culture medium only. After 4 hours, culture medium was removed, and 2 ml of DMEM containing 10% FBS was added to the cells, which were then further incubated for 2 hours under the condition of 37° C. and 5% $CO_2$.

1.3. Verification of Interferon-β Expression

To verify the expression of interferon-β in the cells treated with RNA oligonucleotides described above, RNA was isolated according to the following method.

After removing the culture medium, the cells were recovered with 500 μl of TRI-reagent (Ambion, USA), and chloroform was added to the collected cells to separate the RNA layer. Isopropanol was added thereto to make a pellet, and the pellet was washed with 75% ethanol, dried, and dissolved in sterilized distilled water. The separated RNAs were treated with DNase (Promega, USA) for 30 minutes at room temperature to remove contaminated DNAs, and DNase was inactivated by a stop solution. Then, the resultant was treated with Superscript III Reverse Transcriptase (In-vitrogen, USA) for 1 hour at 50° C. to synthesize cDNAs from the RNAs.

Using the synthesized cDNAs as a template, real-time PCR was carried out. Specifically, real-time PCR was carried out by mixing h-tag DNA polymerase (solgent, Republic of Korea), dNTP, tetraethylammonium chloride, evagreen dye (Biotium, USA), and primers for interferon-β target gene and GAPDH reference gene. Real-time PCR was performed as follows: fixation for 15 minutes at 95° C., then, repeating a set of reactions (20 seconds at 95° C., 40 seconds at 60° C., and 20 seconds at 72° C.) for 40 cycles. The primers for interferon-β and GAPDH are shown in Table 1 below.

TABLE 1

| SEQ ID NO | Name | Sequence |
| --- | --- | --- |
| SEQ ID NO: 11 | Interferon-β forward | 5'-ggaggacgccgcattgac-3' |
| SEQ ID NO: 12 | Interferon-β reverse | 5'-caatagtctcattccagccagtgc-3' |
| SEQ ID NO: 13 | GAPDH forward | 5'-gcattgccctcaacgaccac-3' |
| SEQ ID NO: 14 | GAPDH reverse | 5'-gaggccatgtgggccatgag-3' |
| SEQ ID NO: 15 | ISG56 forward | 5'-gcctccttgggttcgtctacaa-3' |
| SEQ ID NO: 16 | ISG56 reverse | 5'-tcaaagtcagcagccagtctca-3' |

Figure 3:
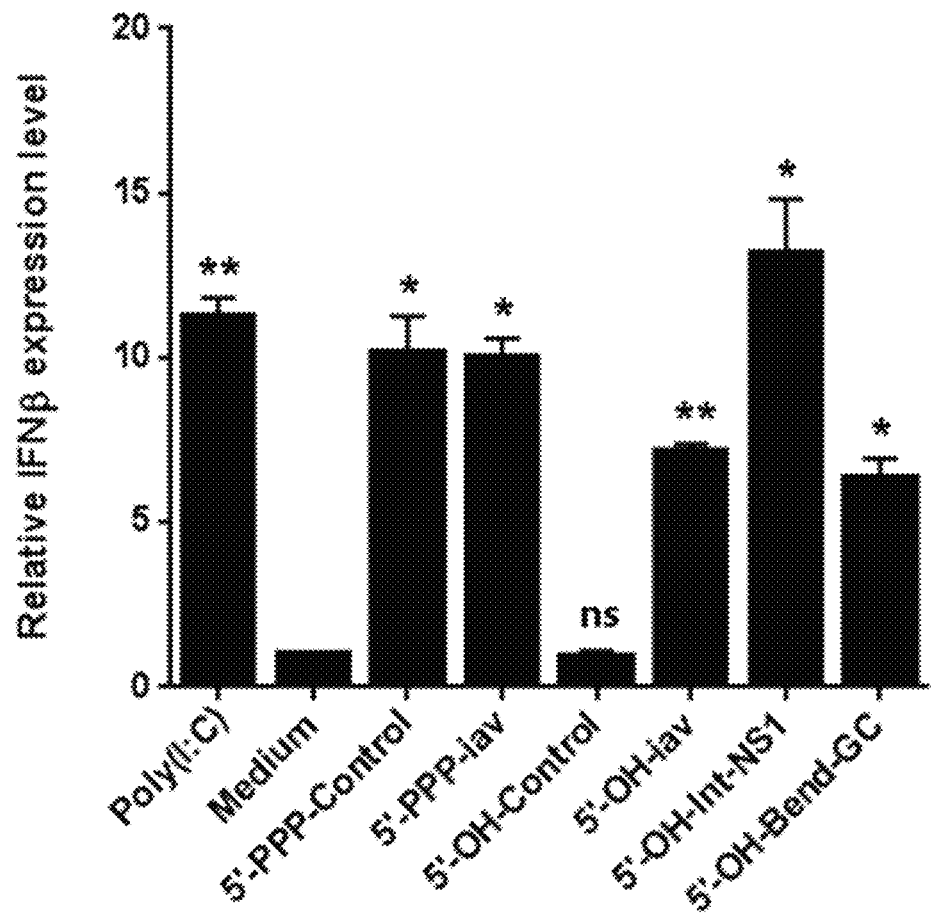
FIG. 3 is a graph showing the increase of interferon-β expression by an RNA oligonucleotides prepared according to one example of the present disclosure.

The changes in the interferon-β expression are shown in the graph of FIG. 3.

As indicated in FIG. 3, it was found that the RNA oligonucleotide having a helical bend structure even with a hydroxy group at the 5'-end as well as the RNA oligonucleotide having a triphosphate group at the 5'-end increased the interferon-β expression to a significant level.

Experimental Example 2: Verification of Interferon-β Expression by Hairpin RNA of Short Length In Experimental Example 1, it was found that RNA oligonucleotides having a helical bend structure increased the interferon-β expression. To elucidate which portion of the RNA oligonucleotides influences the interferon-β expression, a real time PCR was performed by the same method as Experimental Example 1 using 5'-OH-Bend-GC-8bp, which is a shorter hairpin RNA containing a helical bend structure.

The cells for negative control were treated with the culture medium only or 5'-OH-control, while those for positive control were treated with poly (I:C). The cells of experimental groups were treated with 5'-OH-Bend-GC-8bp and 5'-OH-Bend-GC RNA oligonucleotides. The experiments with 5'-OH-Bend-GC-8bp were performed three times.

Figure 4:
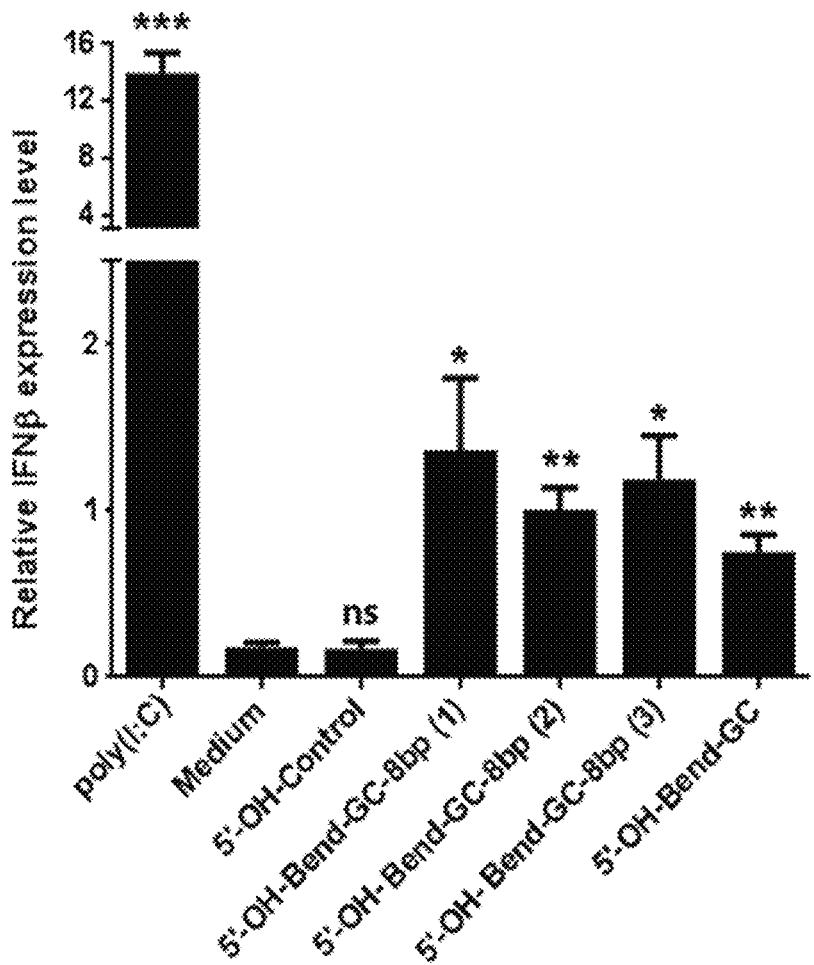
FIG. 4 is a graph showing the increase of interferon-β expression by 5'-OH-Bend-GC-8bp, an RNA oligonucleotide prepared according to one example of the present disclosure.

The changes in the interferon-β expression are shown in the graph of FIG. 4.

As can be seen from FIG. 4, it was found that 5'-OH-Bend-GC-8bp and 5'-OH-Bend-GC increased the interferon-β expression to a significant level.

Experimental Example 3: Verification of ISG56 Expression by Minimum-Length RNA Oligonucleotide To investigate whether 5'-OH-8bp-Bend-GC-Minimum, a double-stranded RNA of minimum length excluding the loop portion of 5'-OH-Bend-GC-8bp verified in Experimental Example 2 can increase interferon-β expression, changes in ISG56 expression induced by interferon-β expression were examined.

All experiments were performed by the same method as Experimental Example 1 using the primers shown in Table 1, except the following. The cells for negative control were treated with the culture medium only or 5'-OH-Cont-GC-8bp having no helical bend structure, while those for positive control were treated with 5'-PPP-Control. The cells of experimental groups were treated with 5'-OH-Bend-GC-8bp and 5'-OH-8bp-Bend-GC-Minimum RNA oligonucleotides.

Figure 5:
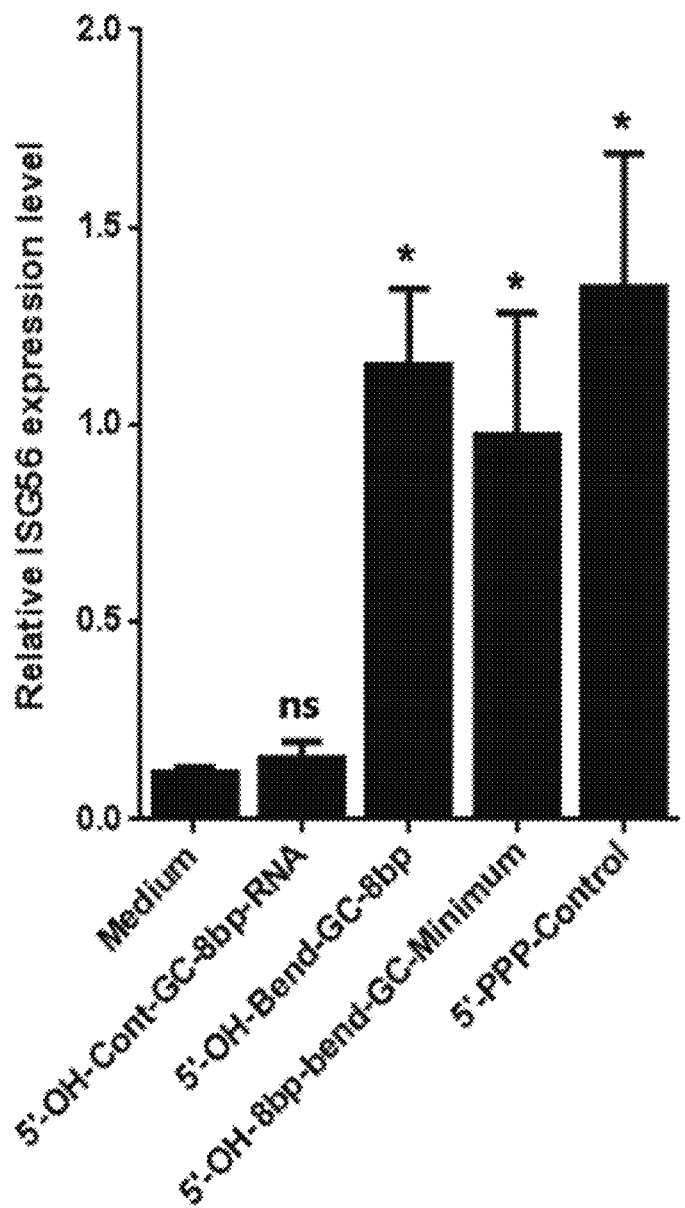
FIG. 5 is a graph showing the increase of ISG56 expression by 5'-OH-8bp-Bend-GC Minimum, an RNA oligonucleotide prepared according to one example of the present disclosure.

The changes in the ISG56 expression are shown in the graph of FIG. 5.

As can be seen from FIG. 5, it was found that 5'-OH-8bp-Bend-GC-Minimum, a double-stranded RNA of minimum length in which the base sequences represented by SEQ ID NO:3 and SEQ ID NO:4 are bound by a complementary binding, increased the ISG56 expression to a significant level.

Experimental Example 4: Verification of ISG56 Expression by RNA Oligonucleotides Connected by Phosphorothioate Bond or Palindromic Structure Among the RNA oligonucleotides having a helical bend structure prepared above, an RNA oligonucleotide in which a phosphodiester bond was substituted with a phosphorothioate bond or an RNA oligonucleotide having two helical bend structures in which two RNA oligonucleotides of minimum length having a helical bend structure are connected by a palindromic structure were tested to examine whether these RNA oligonucleotides can increase the interferon-β expression by assessing changes in the ISG56 expression induced by interferon-β expression.

All experiments were performed by the same method as Experimental Example 1 using the primers shown in Table 1, except the following. The cells for negative control were treated with the culture medium only or 5'-OH-Cont-GC-8bp having no helical bend structure, while those for positive control were treated with 5'-OH-Bend-GC-8bp. The cells of experimental groups were treated with 5'-OH-Bend-GC-8bp-PS and 5'-OH-16mer-Double Bend RNA oligonucleotides.

Figure 6:
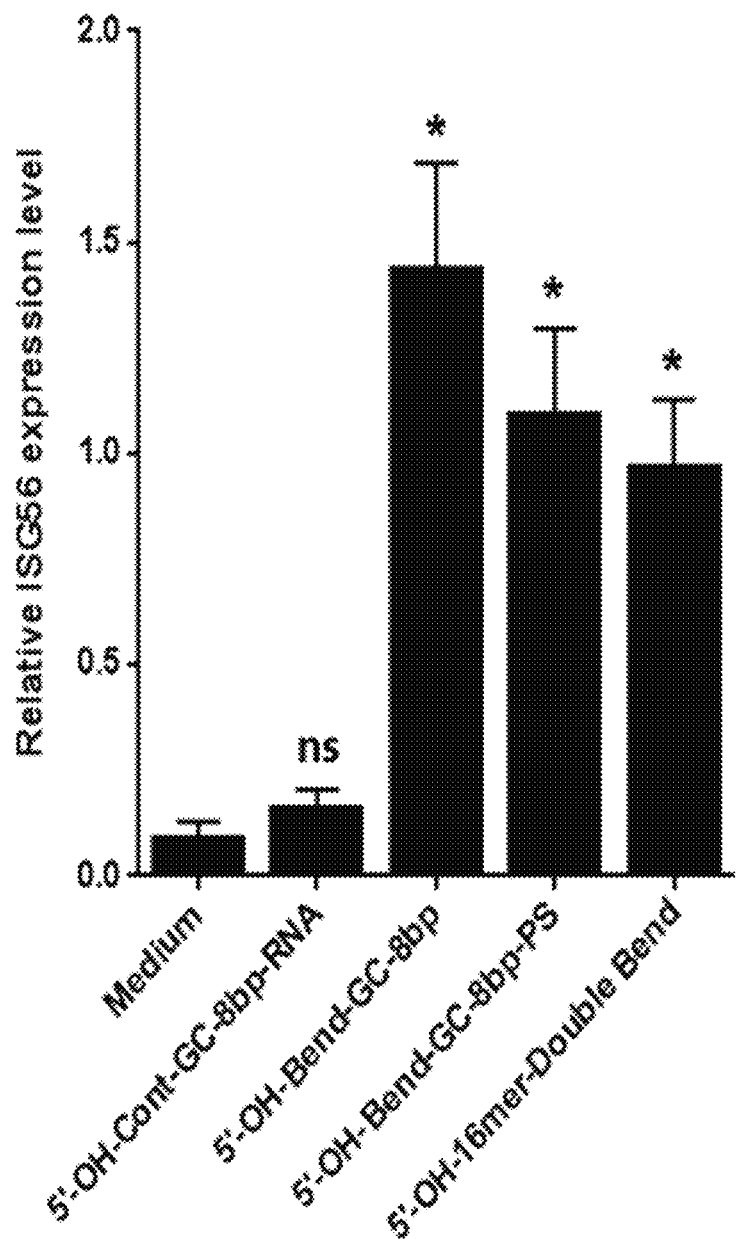
FIG. 6 is a graph showing the increase of ISG56 expression by 5'-OH-Bend-GC-8bp, 5'-OH-Bend-GC-8bp-PS and 5'-OH-16mer-Double Bend, RNA oligonucleotides prepared according to one example of the present disclosure.

The changes in the ISG56 expression are shown in the graph of FIG. 6.

As can be seen from FIG. 6, it was found that 5'-OH-Bend-GC-8bp-PS, an RNA oligonucleotide which has a helical bend structure and a resistance to endonuclease due to the substitution of a phosphodiester bond with a phosphorothioate bond, and 5'-OH-16mer-Double Bend increased the ISG56 expression to a significant level.

Experimental Example 5: Verification of ISG56 Expression by Long RNA Oligonucleotide Among the RNA oligonucleotides having a helical bend structure prepared above, it was examined whether a long-length RNA oligonucleotide can increase the interferon-β expression by assessing changes in the ISG56 expression induced by interferon-β expression.

All experiments were performed by the same method as Experimental Example 1 using the primers shown in Table 1, except the following. The cells for negative control were treated with the culture medium only, while those for positive control were treated with 5'-PPP-iav. The cells of experimental groups were treated with 5'-OH-Long_Bend RNA oligonucleotide.

Figure 7:
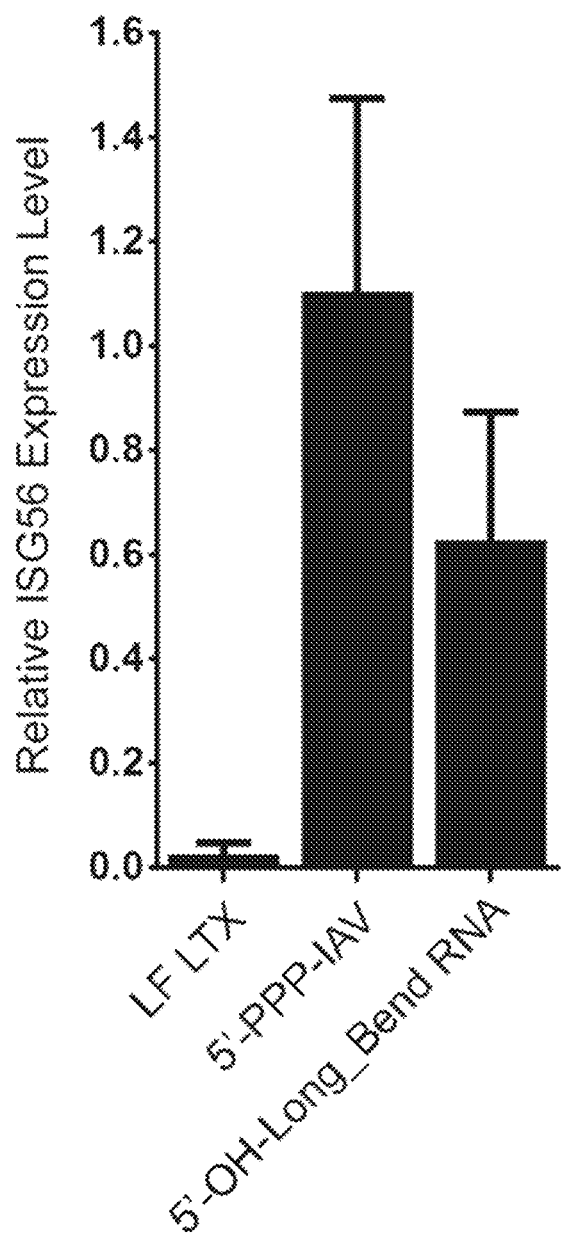
FIG. 7 is a graph showing the increase of ISG56 expression by 5'-OH-Long_Bend, an RNA oligonucleotide prepared according to one example of the present disclosure.

The changes in the ISG56 expression are shown in the graph of FIG. 7.

As can be seen from FIG. 7, it was found that 5'-OH-Long_Bend, a long-length RNA oligonucleotide having a helical bend structure, increased the ISG56 expression to a significant level.

These results indicate that RNA oligonucleotides of the present disclosure which have a helical bend structure showed excellent activity of increasing the expressions of interferon-β and ISG56. As such, these RNA oligonucleotides can be used as an immune system enhancer.

What is claimed is:

1. A double-stranded RNA oligonucleotide comprising the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein:
   the base sequences are bound to each other by a complementary binding to form a double strand having a helical bend structure;
   the base sequences represented by SEQ ID NO:1 and SEQ ID NO:2 have a hydroxy (OH) group at the 5'-end thereof, respectively; and
   wherein $N_1$ to $N_6$ are G or C in the base sequence represented by SEQ ID NO:1 or SEQ ID NO:2.

2. The RNA oligonucleotide of claim 1, wherein $N_1$ is G, $N_2$ is C, and $N_3$ is G in the base sequence represented by SEQ ID NO:1 (corresponding to SEQ ID NO:3); and $N_4$ is C, $N_5$ is G, and $N_6$ is C in the base sequence represented by SEQ ID NO:2 (corresponding to SEQ ID NO:4).

3. The RNA oligonucleotide of claim 1, wherein at least one of the phosphodiester bonds in the RNA oligonucleotide is changed to at least one selected from the group consisting of a phosphorothioate bond, a boranophosphate bond and a methylphosphonate bond.

4. The RNA oligonucleotide of claim 1, wherein the helical bend structure of the double strands is formed between the fourth base (A) of SEQ ID NO:1 and the fifth base (U) of SEQ ID NO:2 when the third base (U) and the fifth base (G) of SEQ ID NO:1 and the sixth base (G) and the fourth base (U) of SEQ ID NO:2 have wobble base pairs, respectively.

5. An immune system enhancer comprising the RNA oligonucleotide of claim 1 as an active ingredient.

6. An RNA oligonucleotide comprising the base sequence represented by SEQ ID NO:1 (5'-$N_1$GUAGA$N_2N_3$-3') and the base sequence represented by SEQ ID NO:2 (5'-$N_4N_5$UUUGC$N_6$-3') wherein:
   the base sequences are bound to each other by a complementary binding to form a double strand having a helical bend structure;
   the 3'-end of the base sequence represented by SEQ ID NO:1 and the 5'-end of the base sequence represented by SEQ ID NO:2 are connected into a loop to form a hairpin structure;
   the base sequence represented by SEQ ID NO:1 has a hydroxy (OH) group directly attached to the 5' carbon thereof;
   wherein $N_1$ to $N_6$ are G or C in the base sequence represented by SEQ ID NO:1 or SEQ ID NO:2.

7. The RNA oligonucleotide of claim 6, wherein $N_1$ is G, $N_2$ is C, and $N_3$ is G in the base sequence represented by SEQ ID NO:1 (corresponding to SEQ ID NO:3); $N_4$ is C, $N_5$ is G, and $N_6$ is C in the base sequence represented by SEQ ID NO:2 (corresponding to SEQ ID NO:4).

8. The RNA oligonucleotide of claim 6, wherein the loop is composed of at least 4 bases.

9. The RNA oligonucleotide of claim 6, wherein the loop is composed of 4 to 80 bases.

10. The RNA oligonucleotide of claim 6, wherein the loop is composed of 4 to 50 bases.

11. The RNA oligonucleotide of claim 8, wherein the loop is composed of UUCG bases.

12. The RNA oligonucleotide of claim 6, wherein the RNA oligonucleotide has a base sequence represented by SEQ ID NO:6, SEQ ID NO:7, SEQ ID NO:8, SEQ ID NO:10 or SEQ ID NO:19.

13. An immune system enhancer comprising the RNA oligonucleotide of claim 6 as an active ingredient.

14. An RNA oligonucleotide consisting of two base sequences, each base sequence represented by SEQ ID NO:17 (5'-$N_1$GUAGAN$_2$N$_3$N$_4$N$_5$UUUGCN$_6$-3') wherein:

the two base sequences represented by SEQ ID NO:17 are bound to each other by a complementary binding to form a double strand having a helical bend structure;

the two base sequences represented by SEQ ID NO:17 have a hydroxy (OH) group at the 5'-end thereof, respectively;

wherein $N_1$ to $N_6$ are G or C in the base sequence represented by SEQ ID NO:17.

15. The RNA oligonucleotide of claim 14, wherein $N_1$ is G, $N_2$ is C, $N_3$ is G, $N_4$ is C, $N_5$ is G, and $N_6$ is C in the base sequence represented by SEQ ID NO:17 (corresponding to SEQ ID NO:18).

16. The RNA oligonucleotide of claim 14, wherein at least one of the phosphodiester bonds in the RNA oligonucleotide is changed to at least one selected from the group consisting of a phosphorothioate bond, a boranophosphate bond and a methylphosphonate bond.

17. An immune system enhancer comprising the RNA oligonucleotide of claim 14 as an active ingredient.

* * * * *